United States Patent
Shim et al.

(10) Patent No.: US 6,533,958 B2
(45) Date of Patent: Mar. 18, 2003

(54) SYSTEM FOR CONTROLLING MICROBIAL FOULING

(75) Inventors: Sang Hea Shim, Seoul (KR); Chung Soo Kim, Kyungki-do (KR)

(73) Assignee: Acculab Co., Ltd., Seoul (KR)

( * ) Notice: Subject to any disclaimer, the term of this patent is extended or adjusted under 35 U.S.C. 154(b) by 0 days.

(21) Appl. No.: 09/950,637

(22) Filed: Sep. 13, 2001

(65) Prior Publication Data

US 2002/0056689 A1 May 16, 2002

Related U.S. Application Data

(62) Division of application No. 09/605,398, filed on Jun. 28, 2000.

(30) Foreign Application Priority Data

Dec. 13, 1999 (KR) .............................................. 99-57299
Jun. 12, 2000 (KR) ........................................ 2000-32103

(51) Int. Cl.$^7$ .................................................. C02F 1/76
(52) U.S. Cl. ........................ 252/176; 210/698; 210/755; 210/756; 210/764; 252/180; 252/181; 422/15; 422/37; 424/661; 424/723
(58) Field of Search .......................... 162/161; 210/698, 210/752, 754, 755, 756, 764; 252/176, 180, 181; 422/15–18, 37; 424/661, 723

(56) References Cited

U.S. PATENT DOCUMENTS

| | | | | |
|---|---|---|---|---|
| 3,328,294 A | | 6/1967 | Self et al. .................... 210/755 |
| 4,759,852 A | * | 7/1988 | Trulear ........................ 210/699 |
| 5,464,636 A | * | 11/1995 | Hight et al. ................. 424/661 |
| 5,503,768 A | * | 4/1996 | Tokuoka et al. ............ 252/189 |
| 5,565,109 A | * | 10/1996 | Sweeny ....................... 162/161 |
| 5,575,945 A | * | 11/1996 | Perlman ..................... 210/756 |
| 5,795,487 A | | 8/1998 | Dallmier et al. ............ 210/754 |
| 5,976,386 A | * | 11/1999 | Barak ......................... 210/101 |
| 6,110,387 A | * | 8/2000 | Choudhury et al. ........ 210/752 |
| 6,303,038 B1 | * | 10/2001 | Sanders et al. ............. 210/754 |

* cited by examiner

*Primary Examiner*—Peter A. Hruskoci
(74) *Attorney, Agent, or Firm*—Shanks & Herbert

(57) ABSTRACT

A method of controlling microbial fouling is provided.

The method controls microbial fouling using hypobromous acid, HOBr, formed by the reaction between an aqueous solution of alkali or alkaline earth metal hypochlorite and a bromide ion source.

The method is characterized in that the alkali or alkaline earth metal hypochlorite or/and the bromide ion source is/are stabilized by the addition of a stabilizer before the hypobromous acid is formed by the reaction there between.

4 Claims, No Drawings

SYSTEM FOR CONTROLLING MICROBIAL FOULING

The application claims priority to Korean patent application Nos. 1999-57299 filed Dec. 13, 1999 and 2000-32103 filed Jun. 12, 2000 and is a divisional application of U.S. Pat. No. 09/605,398 filed Jun. 28, 2000.

FIELD OF THE INVENTION

The present invention relates to a method of controlling microbial fouling and a control system therefor, more specifically a method of controlling microbial fouling using bromination method wherein hypobromous acid, HOBr, formed by the reaction between hypochlorous acid and bromide ion, is used for controlling the microbial fouling in aqueous system, and a control system therefor.

BACKGROUND OF THE INVENTION

In aqueous system such as cooling water towers, industrial water system, paper processing water and oil field waters, microorganisms including bacteria, fungi and algae may cause biological problems including microbiologically influenced corrosion. In addition, the microorganisms form slime. These microbiologically influenced corrosion and slime formation may deteriorate structures, reduce cooling efficiency, change colors as well as increase environmental and health problems.

Generally, methods using oxidizing biocides and non-oxidizing biocides have been used to control microbial fouling in aqueous systems.

Oxidizing biocides sterilize microorganisms by oxidizing cell proteins while non-oxidizing biocides sterilize microorganisms by inhibiting metabolism.

Examples of such non-oxidizing biocides include isothiazolone, methylenebisisocyanate, glutaraldehyde, quartanary ammonium, and the like.

Generally the biocidal power of non-oxidizing biocides is not comparable with that of oxidizing biocides, but the biocidal activity of non-oxidizing biocides lasts longer than that of oxidizing biocides.

The method using oxidizing biocides includes chlorination method and bromination method, and each reaction mechanism is as follows;

Chlorination

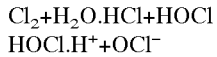

$HOCl.H^+ + OCl^-$

Bromination $HOCl + Br^- \rightarrow HOBr + Cl^-$

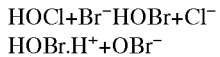

The produced HOCl and OCl⁻ in chlorination, and HOBr and OBr⁻ function as biocides. In chlorination, the concentration of HOCl and OCl⁻ vary depending on pH. As pH increases, the concentration of HOCl decrease more rapidly than that of OCl⁻ as HOCl is more effective as a biocide than OCl⁻, the chlorination becomes less effective in the system having the pH higher than 7.

Further in chlorination method, the ammonia or amine compound contained in an aqueous system such as cooling water may react with HOCl or OCl⁻ to form chlorinated amines which is less effective as biocide, resulting in a reduction of biocidal power.

On the other hand, in bromination method, the concentration of HOBr can still be maintained even in high pH system, and thus, the biocidal power is not reduced.

Further the brominated amine formed by the reaction with ammonia in aqueous system exerts almost same biocidal power as HOBr.

Thus the bromination method is effective compared to the chlorination method.

As a HOCl or OCl⁻ source in both method, alkali or alkaline earth metal hypochlorites, for example sodium hypochlorite (NaOCl) are widely used to control microbial foule in various kinds of aqueous system including cooling water towers, bleaching process, swimming pools, petroleum industry.

However, the alkali or alkaline earth metal hypochlorite is not stable under typical storage conditions and several methods have been suggested to stabilize NaOCl. One of them was suggested in U.S. Pat. No. 3,328,294 to Self.

The '294 patent teaches to stabilize the unstable NaOCl by reacting with an equal molar ratio of sulfamic acid.

Hypobromite having various advantages over hypochlorite such as better biocidal performance in high pH or amine environments and lower volatility also have the unstable problems under typical storage conditions.

U.S. Pat. No. 5,795,487 (corresponding to Korea Patent Applications number 97-708350)(hereinafter referring to as simply '487 patent) assigned to NALCO Chemical Company disclosed a process to manufacture stabilized alkali or alkaline earth metal hypobromite.

The method comprises the steps of: mixing an aqueous solution of alkali or alkaline earth metal hypochlorite with a water soluble bromide ion source; allowing the bromide ion source and the alkali or alkaline earth metal hypochlorite to react to form unstable alkali or alkaline earth metal hypobromite; and adding to the unstable solution of alkali or alkaline earth metal hypobromite an alkali metal sulfmate as stabilizer.

In the '487 patent, the inventors emphasized that the surprisingly increased stability of the stabilized sodium hypobromite achieved by patent method is basically due to the specific order of reagent addition in the process of manufacture, that is, in the order of an aqueous solution of alkali or alkaline earth metal hypochlorite, a water soluble bromide ion source and an aqueous solution of an alkali metal sulfamate. In addition, '487 patent teaches that addition of the stabilizer prior to bromide oxidation would not permit the formations of NaOBr because NaOBr is synthesized by the reaction formula NaOCl+NaBr→NaOBr+NaCl.

However since in the '487 patent the aqueous solution of hypochlorite reacts with an equal molar ratio of the bromide ion source which is expensive on the basis of the above reaction formula, the method according to the '487 patent is costly and requires continuous supply of bromide ion source to maintain the biocidal power in the system.

An object of the present invention is to provide an economic method of controlling microfouling in aqueous system using a stabilized hydrobromite.

Another object of the present invention is to provide an efficient method of controlling microfouling in aqueous system having low volatility, a high free halogen residual long-lasting biocidal power.

It is an object of the present invention to provide a method for preparing a stabilized aqueous alkali or alkaline earth metal hydrobromite solution to be used for the above method.

Further another object of the present invention is to provide an improved anti-microfouling system.

SUMMARY OF THE INVENTION

We have been studying an efficient method of controlling microbiofouling in aqueous system using an aqueous hypochlorite solution, water soluble bromide ion source, metal sulfamate as stabilizer, and unexpectedly found that addition of the stabilizer prior to bromide oxidation could permit the formation of NaOBr, which is contrary to the teaching of the '487 patent.

Specifically, soon after the stabilizer has been added to an aqueous solution of alkali or alkaline earth metal hypochlorite prior to the formation of hypobromite (NaOBr), the stabilized hypochlorite did not react with the water soluble bromide ion source and thus did not allow the NaOBr formation, which met with the teaching of the '487 patent.

However it has been surprisingly found that several to several tens hours after the stabilized hypochlorite and bromide ion source have been added to into aqueous system, the concentration of free halogen residual begun to dramatically increase and the biocidal power lasted long.

Based on the above discovery the inventors continued to study and completed the present invention.

The main feature of the present invention is to allow hypochlorous acid, HOCl, to react with a stabilizer before hypobromites have been formed by the reaction between the hypochlorous acid and a water soluble bromide source in controlling microbial fouling in aqueous system using hypobromite produced by the reaction of hypochlorite and bromide ion source.

In one embodiment of the invention, when alkali or alkaline earth metal hypochlorite is used as a hypochlorous acid source, it is preferred to stabilize the hypochlorite by reacting with a stabilizer and then to allow the stabilized hypochlorite to contact a water soluble bromide ion source to form hypobromites.

However since the hypochlorites preferentially react with the stabilizer than with the bromide ion source, the hypochlorite, the stabilizer and the bromide ion source may simultaneously be added to an aqueous system to be treated.

Also it may be acceptable to mix the stabilizer with the bromide ion source first, and then to allow the mixture to contact the hypochlorite to form hypobromite.

The main features of the present invention is not to allow hypochlorites to react with a water soluble bromide ion source before the hypochlorite has been stabilized.

Such characteristic features of the present invention is definitely distinguished from those of the '487 patent wherein an aqueous solution of alkali or alkaline earth metal hypochlorite is allowed to react with a water soluble bromide ion source to form unstabilized solution of alkali or alkaline earth metal hypobromite, and the addition of stabilizer is followed.

Resultantly the present invention has various advantages over the '487 patent such as less consumption of bromide ion source which is expensive.

Gaseous chlorine can also be used in the present invention as a hypochlorous acid source.

A first aspect of the present invention provides a method for controlling microbial fouling using hypobromous acid, HOBr, formed by the reaction between hypochlorous acid and a bromide ion source, wherein the method comprises the steps of stabilizing the hypochlorous acid by reacting with a stabilizer and then allowing the stabilized hypochlorous acid to react with a water soluble bromide ion source to form hypobromous acid.

A second aspect of the present invention provides a method of controling microbial fouling in aqueous system comprising:
(a) mixing an aqueous solution of alkali or alkaline earth metal hypochlorite having from about 5 percent to about 70 percent of active chlorine with a stabilizer selected from the group consisting of amide derivatives of carbonic acid, hydrogen cyanide, carboxylic acid, amino acid, sulfuric acid, phosphoric acid and boric acid in a molar ratio of stabilizer to alkali or alkaline earth metal hypochlorites of from 1:9 to 9:1 to form a stabilized alkali or alkaline earth metal hypochlorites: and
(b) consecutively or simultaneously applying the stabilized alkali or alkaline earth metal hypochlorites formed in the above step (a) and a water soluble bromide ion source selected from the group consisting of sodium bromide, potassium bromide, lithium bromide, hydrobromic acid, and mixtures thereof into a locus of microorganism to protect.

The stabilized alkali or alkaline earth metal and the bromide ion source can be applied to the microorganism locus in a quantity to maintain the level of free halogen residual within a range between 0.05~10 ppm.

A third aspect of the present invention provides a method of controlling microbial fouling in aqueous system which comprises:
(a) preparing on aqueous solution of alkali or alkaline earth metal hypochlorites having from about 5 percent to about 70 percent of active chlorine:
(b) mixing a water soluble bromide ion source selected from the group consisting of sodium bromide, potassium bromide, lithium bromide, hydrobromic acid and mixture, thereof, and a stabilizer selected from the group consisting of amide derivatives of carbonic acid, hydrogen cyanide, carboxylic acid, amino acid, sulfuric acid, phosphoric acid, and boric acid to prepare a mixture of bromide ion source and stabilizer; and
(c) consecutively or simultaneously applying the aqueous solution of alkali or alkaline earth metal hypochlorites prepared in the above step (a) and the mixture of bromide ion source and stabilizer into a locus of microorganism to protect in a quantity to maintain the level of free halogen residual within a range between 0.05~10 ppm.

A fourth aspect of the present invention provides an anti-microbial fouling system comprising:
an aqueous solution pack of stabilized alkali or alkaline earth metal hypochlorite including an aqueous solution of alkali or alkaline earth metal hypochlorite having from about 5 to 70% of active chlorine and an aqueous solution of stabilizer selected from the group consisting of urea, thioureas, creatinine, cyanuric acids, alkyl hydantoins, mono- or di-ethanolamine, organic sulfonamides, biuret, sulfamic acid and salts thereof, organic sulfamic acid and melamine in a quantity to provide a molar ratio of stabilizer to alkali or alkaline earth metal hypochlorite of 1:9~9:1; and a pack containing water soluble bromide ion source selected from the group consisting of sodium bromide, potassium bromide, lithium bromide, hydrobromic acid and mixtures thereof.

A fifth aspect of the present invention provides an anti-microbial fouling system comprising:
a first pack containing an aqueous solution of alkali or alkaline earth metal hydrochlorites having about 5~70% of active chlorine, and
a second pack containing a mixture of stabilizer selected from the group consisting of urea, thiourea, creatinine, cyanuric acids, alkylhydantoins, mono- or di-ethanolamine, organic sulfonamides, biuret, sulfamic acid and salts thereof, organic sulfamic acid and melanine, and water soluble bromide ion source selected from the group consisting of sodium bromide, potassium bromide, lithium bromide, hydrobromic acid and the mixture thereof, and wherein the molar ratio of the stabilizer to the alkali or alkaline earth metal hypochlorite is 1:9~9.1.

A sixth aspect of the present invention provides an anti-microbial fouling system prepared by:

forming an aqueous solution of stabilized hydrochlorite by adding to an aqueous solution of alkali or alkaline earth metal hydrochlorite a stabilizer selected from the group consisting of amide derivatives of carbonic acid, hydrogen cyanide, carboxylic acids, amino acids, sulfuric acid, phosphoric acid and boric acid in a sufficient amount to stabilize the aqueous solution of alkali or alkaline earth metal hypochlorite; and then adding to the stabilized hydrochlorite a bromide ion source selected from the group consisting of sodium bromide, potassium bromide, lithium bromide, and hydrobromic acid with the molar ratio of the bromide ion source to the stabilized hypochlorite being in a range between 1/10~1.

A seventh aspect of the present invention provides a method of controlling microbial fouling which comprises:

applying an aqueous solution of alkali or alkaline earth metal hypochlorite having from about 5 to 70 percent of active cholorine, a stabilizer selected from the group consisting of urea, thiourea, creatinines cyanuric acids, alkylhydantions, mono- or di-ethanolamine, organic sulfonamides, biuret, sulfamic acid and salts thereof, organic sulfamic acid and melamine in an amount to provide a molar ratio to the alkali or alkaline earch metal hypochlorite of 1:9~9:1, and a water soluble bromide ion source selected from the group consisting of sodium bromide, potassium bromide, lithium bromide, hydrobromic acid and mixture thereof into a locus of microorganism to protect, in a quantity to maintain the level of free halogen residual within a range between 0.05~10 ppm, in the order that the stabilizer is applied first to the locus or is applied between the application of the aqueous solution of alkali or alkaline earth metal hypochlorite and the water soluble bromide ion source or is applied simultaneously with the aqueous solution of alkali or alkaline earth metal hydrochlorite and the water soluble bromide ion source.

A eighth aspect of the present invention provides a method of controlling microbial fouling which comprises:

applying gaseous chloride, a stabilizer selected from the group consisting of urea, thioureas, creatinine, cyanuric acids, alkylhydantoins, mono- or di-diethanolamine, organic sulfonamides, biuret, sulfamic acid and salts thereof, organic sulfamic acid and melamine, and a water soluble bromide ion source selected from the group consisting of sodium bromide, potassium bromide, lithium bromide, hydrobromic acid and mixtures thereof, into a locus of microorganisms in a quantity to maintain the level of free halogen residual within a range between 0.05~10 ppm, in the order that the stabilizer is applied first to the locus or is applied between the application of the gaseous chlorine and the water soluble bromide ion source or is applied simultaneously with the gaseous chlorine and the water soluble bromide ion source.

DETAILED DESCRIPTION OF THE INVENTION

The first aspect of this invention provides a method for controlling microbial fouling using hypobromous acid (HOBr) formed by the reaction between hypochlorous acid (HOCl) and a water soluble bromide ion source (Br⁺), characterized in that an aqueous solution of alkali or alkaline earth metal is stabilized with adding a stabilizer before hypobromous acid is formed by the reaction between the hypochlorous acid and the bromide ion source.

The above characteristic features of this invention distinguish from the '487 patent wherein an aqueous solution of alkali or alkaline earth metal hypochlorite is allowed to react first with a water soluble bromide ion source to form unstabilized solution of alkali or alkaline earth metal hypobromide, and them the addition of stabilizer is followed.

In the present invention wherein hypochlorous acid is stabilized by the addition of the stabilizer and after that the bromide ion source is added to the stabilized hypochlorous, the stabilized hyochlorous acid is believed to function as a reservoir to provide $Br^+$ion from the bromide ion source with HOCl in order to form HOBr which sterilizes microorganis in an aqueous system to protect and is decomposed by ultraviolet rays and recycled for further use as schematically shown below.

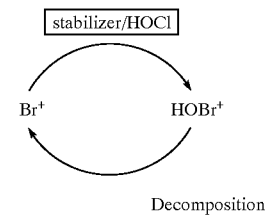

Decomposition

Thus according to the present invention the expensive bromide compound is consumed in a small quantity, while in the prior art the expensive bromide compound is consumed in a large quantity since an aqueous solution of hypochlorite reacts with an equal molar ratio of a bromide ion source on the basis of the formula NaOCl+NaBr.NaOBr+NaCl.

As previously discussed, according to the present invention the addition of the stabilizer to the hypochlorous acid should be carried out prior to bromide oxidation, which has never been disclosed or taught in any prior arts including '487 patent.

In other words, prior arts including '487 patent is based on the fixed idea that already stabilized hypochlorous acid (hypochlorites) do not react with bromine ion, while the present invention is based on the foundings that already stabilized hypochlorous acid reacts with bromine ion several to several tens hours after they have been applied into an aqueous system to protect depending on the temperature of the system and the biocidal activity lasted long time.

Actually the inventors found that hypobromous acid was formed several hours after at a system temperature of 35, and 24 hours after at room temperature.

As hypochlorous acid sources, alkali or alkaline earth metal hypochlorites may be preferably used in the present invention. Gaseous chlorine may also be used as a hypochlorous acid source.

To form hydrochlorous acid, gaseous chlorine or alkali/alkaline earth metal hypochlorites may be introduced into the aqueous system to treat or protect to react with water.

The second aspect of the present invention provides a method of controlling microbial fouling in aqueous system, characterized in that the method comprising mixing a specific aqueous solution of alkali or alkaline earth metal hypochlorites as hypochlorous acid source with specific stabilizers to prepare stabilized hypochlorites, and then consecutively or simultaneously applying the stabilized hypochlorites and bromide ion source into a locus of microorganism to protect.

This aspect of the present invention, as is in the first aspect, also has advantages over the prior art such as less consumption of expensive bromide ion source, long-lasting biocidal activity.

Characteristic features of the third aspect of the present invention is to mix stabilizer with bromide ion source instead of mixing with aqueous solution of alkali or alkaline earth metal hypochlorites in the second aspect.

Namely, according to the method of the second aspect, the hypochlorites is stabilized with stabilizer before bromide ion source is added, but in the third aspect bromide ion source is mixed with stabilizer and the mixture and hypochlorites is consecutively or simultaneously applied into a locus of microorganism to protect.

In this case, when the hypochlorites is applied into a aqueous system, the stabilizer in the mixture preferentially react with the hypochlorite to form stabilized hypochlorite which results in same effect as in the second aspect.

The fourth aspect of the present invention provides an anti-microbial fouling system comprising a first pack containing an aqueous solution of stabilized hypochlorite and a second pack containing bromide ion source.

The characteristic features of the fifth aspect is to mix stabilizer with bromide ion in a pack.

The sixth aspect of the present invention provides an anti-microbiofouling system which enables to storage the stabilized hypochlorite and the bromide ion source in a pack.

Even when the stabilized hypochlorite and bromide ion source are stored in same pack in concentrate state, the chlorites and bromide ion source do not react each other so long as they are stored in a pack in concentrate state.

However when the stabilized hypochlorite and bromide ion source are introduced into a dilute aqueous system of microorganism locus, they begin to react to form hypobromous acid having biocidal activity.

The seventh aspect of the present invention provides a method of controlling microbial fouling, comprising applying an aqueous solution of hypochlorites, stabilizer and bromide ion source in a specific order.

With specifying the order of addition (application), direct reaction between unstabilized hypochlorites and bromide ion source could be prevented, and the stabilization of hypochlorites is preceded.

In the eighth aspect of the present invention, gaseous chlorine is used as an hypochlorous acid source.

When gaseous chlorine is introduced into a locus of microorganism, the gaseous chlorine reacts with water to form hypochlorous acid.

Each component used in this invention will be discussed hereinafter.

The alkali or alkaline earth metal hypochlorite which is useful in this invention is selected from the group consisting of sodium hypochlorite, potassium hypochlorite, lithium hypochlorite, magnesium hypochlorite and calcium hypochlorite.

The alkali or alkaline earth metal hypochlorite preferably contains about 5~70% of chlorine as active halogen.

The hypochlorite having less than 5% of chlorine is commercially invalid and the hypochlorite having more then 70% of chlorine is hard to commercially manufacture.

The bromide ion source useful in this invention is selected from the group consisting of sodium bromide, potassium bromide, lithium bromide and hydrobromic acid.

In a preferred embodiment, the bromide ion source is sodium bromide. The stabilizer in this invention includes amide derivatives of carbonic acid, hydrogen cyanide, carboxylic acid, amino acid, sulfuric acid, phosphoric acid, and boric acid.

Examples of those stabilizer are urea, thiourea, creatinine, cyanuric acids, alkyl hydantoins, mono- or di-ethanolamine, organic sulfonamides, biuret, sulfamic acid and salts thereof, organic sulfamic acid and melamine. Sulfamic acid is preferred from the economic and efficiency view point.

The amount of hypochlorite used will vary depending upon the kinds of hypochlorite used and the degree and extent of contaminated by microbial fouling.

When an aqueous system is severely contaminated, the initial quantity of hypochlorite is preferably increased.

The molar ratio of the stabilizer to the alkali or alkaline earth metal hypochlorite is 1:9 to 9:1.

And the amount of bromide ion source used to the stabilized hypochlorite will vary depending upon the degree and extent contaminated by microorganism.

A typical molar ratio of bromide ion source to the stabilized hypochlorite is 1/10~1 mol.

For example, when the concentration of the stabilized hypochlorite is 10 ppm, the concentration of the bromide ion source could be no less then 1 ppm.

Therefore the expensive bromide ion source, in the present invention, is less consumed than in the prior arts wherein equal molar ratio of the expensive bromide ion source to the hypochlorite is required.

Though the concentrations of the stabilized hypochlorites and the bromide ion source in aqueous system to protect vary depending on the aqueous system, the level of free halogen residual in the system is preferably between 0.05~10 ppm, more preferably between 0.1~5 ppm, and most preferably 0.2~2 ppm.

The anti-microbial fouling system according to the present invention may contain any of the conventional corrosion and scale inhibitors known in the art.

The corrosion inhibitor includes anodic corrosion inhibitor such as chromates, nitrites, orthophosphates, silicates and molybdtes, cathodic corrosion inhibitor such as zinc, polyphosphates, and phosphonates, and copper corroision inhibitor such as mercaptobenzothiazole, benzotriazole and tolytriazole.

The scale inhibitor includes organo phosphates and acrylic polymers.

Examples of the organo phosphates include triethanolamine phosphate (TEAP), aminotrismethylene phosphonic acid (AMP), 1-hydroxyethylidene-1,1-diphosphonic acid (HEDP), 2-phosphonobutane-1,2,4-tricarboxylic acid (PBTC).

The acrylic polymer may include homo-acrylic polymer, co-acrylic polymer and ter-acrylic polymer.

The method and system according to this invention can be widely applied to any aqueous system where inhibition of the growth of microorganism is required.

The aqueous system include, but are not limited to: cooling water tower, air cleaner, swimming pool, spas, industrial water system, laundry detergents, bleaching agent, oil field water, sweet water, gas scrubber system, recycling water system and water slide.

Any conventional pH modifier can be added to the aqueous solution of alkali or alkali earth metal hypochlorites and may include, but are not limited to, sodium hydroxide, potassium hydroxide, magnesium hydroxide, lithium hydroxide and calcium hydroxide.

The following examples are presented to illustrate further various aspect of the present invention, but are not intended to limit the scope of this invention in any aspect.

EXAMPLE 1

Free Halogen Residual

Sample 1 to 3 was added into an aqueous system in an amount of 5 ppm based on NaOCl and the change of free halogen residual concentration in the system was measured for 8 days.

Results of the tests are shown below table 1.

TABLE 1

| | ppm | | | | | | | |
|---|---|---|---|---|---|---|---|---|
| | 1 | 2 | 3 | 4 | 5 | 6 | 7 | 8 |
| 1* | 0.04 | 0.11 | 0.03 | 0.02 | 0.04 | 0.03 | 0.02 | 0.02 |
| 2* | 0.67 | 0.77 | 0.65 | 0.24 | 0.07 | 0.03 | 0.03 | 0.02 |
| 3* | 0.16 | 2.34 | 1.70 | 1.62 | 1.12 | 0.73 | 0.43 | 0.05 |

Sample 1* sulfamic acid was added into NaOCl solution
Sample 2* equal molar ratio of NaOCl and NaBr were mixed and followed by addition of sulfamic acid, as suggested in '487 patent
Sample 3* same amount of NaOCl as in sample 1 and 2 was mixed with sulfamic acid, and the mixture was applied into an aqueous system to protect, and addition of same amount of NaBr as in sample 2 was followed As shown in the Table 1, the stabilized NaOCl(sample 1) released few free halogen residual.

And sample 2 prepared by the method suggested by '487 patent showed high concentration of free halogen residual until 2nd day after but the concentration was rapidly decreased from 3rd day.

Sample No 3 prepared by the method according to the present invention showed low concentration of free halogen residual on the first day of addition, however from the second day the concentration of free halogen residual was dramatically increased and lasted to the 7th day.

These results demonstrate high efficiency of the method and system of this invention.

With the same molar ratio and components, the higher concentration of free halogen residual was accomplished and it lasted longer than 2 times compared to the prior art.

The concentration of free halogen residual in the present invention was changed from 2.34(second day) to 0.43(7th day), while in the '487 patent from 0.77 to 0.03.

Thus the present invention requires less consumption of expensive bromide ion source than required by the prior art, and additionally more improved performance due to higher concentration can be attained.

EXAMPLE 2

Activity Against Microorganism

Tests were conducted to determine the activity of the inventive system and method against bacteria.

To polluted water containing 103 bacteria were added 10 ppm of sample 4 and 5 based on NaOCl, respectively.

After 48 hours, 20 ppm of sample 4 and 5 were additionally added and concentrations of free halogen residual and the number of bacteria alive were measured.

Results of this test are shown below.

TABLE 2

| | | UNIT: ppm | | | | | |
|---|---|---|---|---|---|---|---|
| | | days | | | | | |
| | | 1 | 2 | 3 | 4 | 5 | 6 |
| Sample 4* | Halogen residual | 0.33 | 0.03 | 0.16 | 0.11 | 0.14 | 0.09 |
| | No. of bacteria | $10^2$ | $10^2$ | $10^1$ | $10^1$ | $10^2$ | $10^2$ |
| Sample 5* | Halogen residual | 0.05 | 0.08 | 0.14 | 0.73 | 0.67 | 0.28 |
| | No. of bacteria | $10^4$ | $10^3$ | $10^2$ | $10^1$ | $10^0$ | $10^0$ |

Sample 4 sulfamic acid was introduced after NaOCl and NaBr were mixed according to the teachings of '487 patent
Sample 5 According to the present invention, NaOCl was mixed with sulfamic acid, and then the mixture was introduced to the aqueous system to be treated.
After that, equal amounts of NaBr to the sample 4 were added into the aqueous system As table 2 shows, Sample No. 4 prepared by the teaching of '487 patent had better biocidal power on the same day the mixture was introduced, compared to sample 5 prepared according to the present invention.

But 24 hours later, the biocidal power was suddenly decreased and even on the sixth day formation of mess was visually observed in the aqueous system.

On the other hand, Sample No. 5 prepared according to the present invention continuously demonstrated long-lasting and better anti-fouling activities. No moss was visually found in the aqueous system.

EXAMPLE 3

Efficiency Against Moss

To polluted water in which algae were floating were added sample 6 and 7 in an amount to provide each 20 ppm concentration.

The concentration of free halogen residual and the condition of alage in the polluted aqueous system were observed.

The change of free halogen concentration is set forth in Table 3.

TABLE 3

| | UNIT: ppm | | | | | |
|---|---|---|---|---|---|---|
| | days | | | | | |
| no | 1 | 2 | 3 | 4 | 5 | 6 |
| 6 | 0.98 | 0.74 | 0.35 | 0.12 | 0.07 | 0.03 |
| 7 | 0.24 | 2.12 | 2.42 | 1.48 | 1.28 | 1.16 |

Sample 6: Sulfamic acid was introduced after NaOCl and NaBr were mixed, according to the teachings of '487 patent
Sample 7: According to the present invention, NaOCl was mixed with sulfamic acid and then the mixture was introduced into the aqueous system to be treated. After that, equal amount of NaBr to the sample 4 were added into the aqueous system.

As shown in Table 3, the concentration of free halogen of the sample No. 6 prepared by the teaching of '487 patent has been suddenly decreased.

The floating algae were deposited at the bottom and cohesive slime was begun to form.

With the lapse of time, the algae color was changed from light yellowish green to dank green. The number of bacteria was decreased for the first 13 days, but rapidly increased thereafter.

However, Sample No. 7 according to the present invention, prepared by first mixing NaOCl and sulfamic acid to form stabilized NaOCl, applying the stabilized NaOCl to a aqueous system to protect, and then adding NaBr to the system, demonstrated long-lasting biocidal activities and higher biocidal power than in Sample No. 6.

Algae was deposited at the bottom, as was in Sample No. 6, but has not grown any longer, and disappeared 5 days later, bacteria was not observed from 3 days after.

After 30 days storage, very strong slime plugs were formed in sample 6, while any slime has not been found in sample 7.

In addition, Sample No. 6 demonstrated less-effectiveness for algae than for bacteria and funges.

EXAMPLE 4

Effects of NaBr Amount on Free Halogen Residual Concentration

NaOCl was stabilized with sulfamic acid and the stabilized NaOCl was introduced into an aqueous system to be treated and then to the aqueous system was added NaBr.

The change of concentration of free halogen residual depending on the NaBr amount added has been observed for 7 days after the addition.

The date appears in Table 4, below.

TABLE 4

| | | sample 8 | sample 9 | sample 10 |
|---|---|---|---|---|
| | amount of each component | | | |
| Component | NaOC | 10 ppm | 10 ppm | 10 ppm |
| | Sulfamic acid | 10.92 ppm | 10.92 ppm | 10.92 ppm |
| | NaBr | 13.93 ppm | 9.69 ppm | 4.14 ppm |
| | Concentration of Free Halogen Residual (ppm) | | | |
| Time Lapsed | 1 day | 0.16 | 0.09 | 0.05 |
| | 2 days | 2.04 | 1.08 | 0.64 |
| | 3 days | 2.12 | 2.62 | 2.4 |
| | 4 days | 2.42 | 1.66 | 1.52 |
| | 5 days | 1.48 | 1.46 | 1.24 |

TABLE 4-continued

| | sample 8 | sample 9 | sample 10 |
|---|---|---|---|
| 6 days | 1.28 | 1.26 | 1.12 |
| 7 days | 1.16 | 1.11 | 0.92 |

The above Table 4 shows that, according to the present invention, the concentration can be maintained even when the amount of NaBr is decreased. Thus, the amount of expensive bromide ion source can be reduced while maintaining the concentration of free halogen residual.

We claim:

1. An anti-microbiofouling system comprising: an aqueous solution pack of stabilized alkali or alkaline earth metal hypochlorite including an aqueous solution of alkali or alkaline earth metal hypochlorite having from about 5 to 70% of active chlorine and an aqueous solution of stabilizer selected from the group consisting of urea, thiourea, creatinines, cyanuric acid, alkyl hydantoins, mono- or di-ethanolamine, organic sulfonamides, biuret, sulfamic acid and salts thereof, organic sulfamic acid and melamine in a quantity to provide a molar ratio of the stabilizer to the alkali or alkaline earth metal hypochlorite of 1:9~9:1; and a pack containing water soluble bromide ion source selected from the group consisting of sodium bromide, potassium bromide, lithium bromide, hydrobromic acid, and mixtures thereof, wherein the molar ratio of the bromide ion source to the stabilized hydrochlorite is in a range between 1/10–1.

2. The system according to claim 1 wherein the alkali or alkaline earth metal hypochlorite is selected from the group consisting of sodium hypochlorite, potassium hypochlorite, lithium hypochlorite, magnesium hypochlorite, calcium hypochlorite, and mixtures thereof.

3. The system according to claim 1, wherein the pack containing water soluble bromide ion source also contains corrosion and/or scale inhibitors.

4. The system according to anyone of claims 1 to 3, wherein the alkali or alkali earth metal hypochlorite is sodium hypochlorite, and the bromide ion source is sodium bromide, and the stabilizer is sulfamic acid.

* * * * *